(12) United States Patent
Carroll

(10) Patent No.: US 6,482,796 B2
(45) Date of Patent: Nov. 19, 2002

(54) THERAPEUTIC USES OF N-TERMINAL BPI PROTEIN PRODUCTS IN ANCA-POSITIVE PATIENTS

(75) Inventor: Stephen Fitzhugh Carroll, Walnut Creek, CA (US)

(73) Assignee: Xoma Corporation, Berkeley, CA (US)

(*) Notice: Subject to any disclaimer, the term of this patent is extended or adjusted under 35 U.S.C. 154(b) by 0 days.

(21) Appl. No.: 09/255,245

(22) Filed: Feb. 22, 1999

(65) Prior Publication Data

US 2002/0119918 A1 Aug. 29, 2002

Related U.S. Application Data

(63) Continuation of application No. 08/742,985, filed on Nov. 1, 1996, now abandoned.

(51) Int. Cl.$^7$ .................................. A61K 38/17
(52) U.S. Cl. ............................. 514/2; 514/12
(58) Field of Search ....................... 514/12, 2

(56) References Cited

U.S. PATENT DOCUMENTS

| | | |
|---|---|---|
| 5,089,274 A | 2/1992 | Marra et al. |
| 5,171,739 A | 12/1992 | Scott et al. |
| 5,198,541 A | 3/1993 | Elsbach et al. |
| 5,234,912 A | 8/1993 | Marra et al. |
| 5,308,834 A | 5/1994 | Scott et al. |
| 5,334,584 A | 8/1994 | Scott et al. |
| 5,348,942 A | 9/1994 | Little, II et al. |
| 5,420,019 A | 5/1995 | Theofan et al. |
| 5,439,807 A | 8/1995 | Grinna et al. |
| 5,447,913 A | 9/1995 | Ammons et al. |
| 5,466,580 A | 11/1995 | White et al. |
| 5,466,581 A | 11/1995 | White et al. |
| 5,484,705 A | 1/1996 | White et al. |
| 5,488,034 A | 1/1996 | McGregor et al. |
| 5,494,896 A | 2/1996 | Hansbrough |
| 5,523,288 A | 6/1996 | Cohen et al. |
| 5,532,216 A | 7/1996 | Espevik et al. |
| 5,576,292 A | 11/1996 | Elsbach et al. |
| 5,578,568 A | 11/1996 | Ammons et al. |
| 5,578,572 A | 11/1996 | Horwitz et al. |
| 5,627,153 A | 5/1997 | Little et al. |
| 5,639,727 A | 6/1997 | Little et al. |
| 5,641,874 A | 6/1997 | Elsbach et al. |
| 5,643,570 A | 7/1997 | Theofan et al. |
| 5,643,875 A | 7/1997 | Friedman et al. |
| 5,646,114 A | 7/1997 | Lambert |
| 5,652,332 A | 7/1997 | Little |
| 5,674,834 A | 10/1997 | Theofan et al. |
| 5,696,090 A | 12/1997 | McGregor et al. |
| 5,703,038 A | 12/1997 | Ammons et al. |
| 5,733,872 A | 3/1998 | Little |
| 5,756,464 A * | 5/1998 | Scannon et al. |

FOREIGN PATENT DOCUMENTS

| | | |
|---|---|---|
| WO | WO 90/09183 | 8/1990 |
| WO | WO 92/03535 | 3/1992 |
| WO | WO 92/09621 | 6/1992 |
| WO | WO 93/05797 | 4/1993 |
| WO | WO 93/06228 | 4/1993 |
| WO | WO 93/23434 | 11/1993 |
| WO | WO 93/23540 | 11/1993 |
| WO | WO 94/17819 | 8/1994 |
| WO | WO 94/18323 | 8/1994 |
| WO | WO 94/20128 | 9/1994 |
| WO | WO 94/20129 | 9/1994 |
| WO | WO 94/20532 | 9/1994 |
| WO | WO 94/21280 | 9/1994 |
| WO | WO 94/25476 | 11/1994 |
| WO | WO 95/00641 | 1/1995 |
| WO | WO 95/01428 | 1/1995 |
| WO | WO 95/02414 | 1/1995 |
| WO | WO 95/08344 | 3/1995 |
| WO | WO 95/08773 | 3/1995 |
| WO | WO 95/10297 | 4/1995 |
| WO | WO 95/19179 | 7/1995 |
| WO | WO 95/19180 | 7/1995 |
| WO | WO 95/19372 | 7/1995 |
| WO | WO 95/19784 | 7/1995 |
| WO | WO 95/20163 | 7/1995 |
| WO | WO 95/24209 | 9/1995 |
| WO | WO 96/01647 | 1/1996 |
| WO | WO 96/08509 | 3/1996 |
| WO | WO 96/21436 | 7/1996 |
| WO | WO 96/30037 | 10/1996 |
| WO | WO 97/04008 | 2/1997 |
| WO | WO 97/17989 | 5/1997 |
| WO | WO 97/17990 | 5/1997 |
| WO | WO 97/42966 | 11/1997 |
| WO | WO 97/42967 | 11/1997 |
| WO | WO 97/44056 | 11/1997 |
| WO | WO 98/06415 | 2/1998 |

OTHER PUBLICATIONS

Burrows, N.P. et al., "ANCA Associated With Behcet's Disease," *J. Royal Society Med.*, 89(1):47P–48P (Jan., 1996).

Dunn, A.C. et al., "Alpha–Antitrypsin Deficiency and Autoantibodies To Bactericidal/Permeability–Increasing Protein (BPI) In Cystic Fibrosis (CF) Lung Disease," Abstracts of the Fourth International Symposium on Clinical Immunology, Jun. 19–22, 1997, Amsterdam, The Netherlands, *The Immunologist*, (Supplement 1), p. 84 (1997) (Abstract 10.0.06).

Elsbach et al., "Seperation and Purification of a Potent Bactericidal/Permeability Increasing Protein and a closely Associated Phospholipase A2 from Rabbit Polymorphonuclear Leukocytes," *J. Biol. Chem.*, 254:11000 (1979).

(List continued on next page.)

Primary Examiner—Gary L. Kunz
Assistant Examiner—Stephen Gucker
(74) Attorney, Agent, or Firm—Marshall, Gerstein & Borun

(57) ABSTRACT

Improved therapeutic uses for N-terminal BPI protein products are described in patients that have BPI-reactive anti-neutrophil cytoplasmic antibodies.

17 Claims, No Drawings

OTHER PUBLICATIONS

Elsbach and Weiss, "Oxygen–Independent Antimicrobial Systems of Phagocytes," In *Inflammation: Basic Principles and Clinical Correlates*, Chapter 30, pp. 603–636, Second Edition, Gallin et al., (Eds.), Raven Press, Ltd., (1992).

Falk et al., "Antigen Specificity of P–ANCA and of C–ANCA," Third Int'l Workshop on ANCA, *Am J. Kidney Dis.*, 18:197 (*Abstract 6*) (1991).

Gazzano–Santoro et al., "High–Affinity Binding of the Bactericidal/Permeability Increasing Protein and a Recombinat Amino–Terminal Fragment to the Lipid A Region of Lipopolysacchride," *Infect. Immun.*, 60(11):4754–4761 (Nov., 1992).

Gray et al., "Cloning of the cDNA of a Human Neutrophil Bactericidal Protein," *J. Biol. Chem.*, 264(16):9505–9509 (Jun. 5, 1989).

Hamilton, M. et al., "Bacterial–Permeability–Increasing Protein (BPI); A Novel Target Antigen For P–ANCA In Inflammatory Bowel Disease," 95th Annual Meteing of the American Gastroenterological Association and Digestive Disease Week, San Diego, California, USA, May 14–17, 1995, *Gastroenterology*, 108(4 Suppl.):A830 (1995).

Herzberg, "Disease Associations of ANCA With Specificity for Bactericidal/Permeability Increasing Protein (BPI)" Abstract presented at 6th Int'l. ANCA Workshop, Lubeck, Germany (1995).

Horwitz et al., Expression and Characterization of Cysteine–Modified Variants of an Amino–Terminal Fragment of Bactericidal/Permeability–Increasing Protein, *Protein Expression Purification*, 8:28–40 (1996).

Kallenberg et al., "Antineutrophil Cytoplasmic Antibodies: A Still–Growing Class of Autoantibodies in Inflammatory Disorders, " *Am. J. Med.*, 93:675–682 (Dec., 1992).

Kallenberg et al., "Anti–neutrophil Cytoplasmic Antibodies: Current Diagnostic and Pathophysiological Potential," *Kidney Int'l.*, 46:1–15 (1994).

Kallenberg et al., "ANCA–Pathophysiology Revisited, " *Clin Exp. Immunol.*, 100:1–3 (1995).

Lambert, L. et al., "Recombinant Bacterial.Permeability–Increasing Protein (rBPI$_{21}$) is Bactericidal In Vitro Against *Pseudomonas aeruginosa* Strains Isolated from Cystic Fibrosis Patients," *XOMA CG 0424: ICAAC*; Toronto, Canada, p. 5.0 (Sep. 28–Oct. 1, 1997) (*Abstract E149*).

Ooi et al., "A 25–kDa NH$_2$–terminal Fragment Carries all the Antibacterial Activites of the Human Neutrophil 60–kDa Bactericidal/Permeability–increasing Protein," *J. Biol. Chem.*, 262(31):14891–14894 (1987).

Ooi et al., "Endotoxin Neutralizing Properties of the 25 kD N–Terminal Fragment of the 55–60 kD Bactericidal/Permeability–increasing Protein of Human Neutrophils," *J. Exp. Med.*, 174:649–655 (Sep., 1991).

Schultz, H. et al., "Use of native and recombinant bactericidal/permeability–increasing proteins (BPI) as antigens for detection of BPI–ANCA," *J. Immunol. Methods*, 205:127–133 (1997).

Stoffel et al., "Anti–neutrophil Cytoplasmic Antibodies (ANCA) Directed Against Bactericidal/Permeability Increasing Protein (BPI): A New Seromarker For Inflammatory Bowel Disease and Associated Disorders," *Clin. Exp. Immunol.*, 104:54–59 (1996).

Stoffel, M.P. et al., "Immunodiagnostic Importance of the BPI–ANCA System, " XIIIth Annual General Meeting British Society for Rheumatolgy, Brighton, England, UK, May 8–10, 1996, *British J. Rheumatology*, 35(Suppl. 1):50 (1996) (Abstract).

Walmsley, R.S. et al., "Antineutrophil cytoplasm autoantibodies against bactericidal/permeability–increasing protein in inflammatory bowel disease," *Gut*, 40:105–109 (1997).

Weiss et al., "Cellular and Subcellular Localization of the Bactericidal/Permeability–Increasing Protein of Neutrophils," *Blood*, 69:652 (Feb., 1987).

Yang, J.J. et al., "Frequency of anti–bactericidal/permeability–increasing protein (BPI) and anti–azurocidin in patients with renal disease," *Clin. Exp. Immunol.*, 105:125–131 (1996).

Zhao et al., "Bactericidal/Permeability–Increasing Protein (BPI) is an Important Antigen for Anti–Neutrophil Cytoplasmic Autoantibodies (ANCA) in Vasculitis," *Clin. Exp. Immunol.*, 99:49–56 (1995).

Zhao et al., "Autoantibodies Against Bactericidal/Permeability–Increasing Protein in Patients with Cystic Fibrosis," *Q.J.M.*, 89(4):259–265 (1996).

Zhao, M.H. et al., "Azurocidin is a novel antigen for anti–neutrophil cytoplasmic autoantibodies (ANCA) in systemic vasculitis," *Clin. Exp. Immunol.*, 103:397–402 (1996).

Zhao, M.H. et al., "A Comprehensive Method to Purify Three Major ANCA Antigens: Proteinase 3, Myeloperoxidase and Bacterial/Permeability–Increasing Protein From Human Neutrophil Granule Acid Extract," *J. Immunol. Methods*, 197:121–130 (Oct. 16, 1996).

* cited by examiner

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
        (A) LENGTH: 1813 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 31..1491

(ix) FEATURE:
        (A) NAME/KEY: mat_peptide
        (B) LOCATION: 124..1491

(ix) FEATURE:
        (A) NAME/KEY: misc_feature
        (D) OTHER INFORMATION: "rBPI"

(xi) SEQUENCE DESCRIPTION: SEQ ID NO:1:

```
CAGGCCTTGA GGTTTTGGCA GCTCTGGAGG ATG AGA GAG AAC ATG GCC AGG GGC         54
                                Met Arg Glu Asn Met Ala Arg Gly
                                -31 -30                     -25

CCT TGC AAC GCG CCG AGA TGG GTG TCC CTG ATG GTG CTC GTC GCC ATA         102
Pro Cys Asn Ala Pro Arg Trp Val Ser Leu Met Val Leu Val Ala Ile
            -20             -15                 -10

GGC ACC GCC GTG ACA GCG GCC GTC AAC CCT GGC GTC GTG GTC AGG ATC         150
Gly Thr Ala Val Thr Ala Ala Val Asn Pro Gly Val Val Val Arg Ile
        -5                   1               5

TCC CAG AAG GGC CTG GAC TAC GCC AGC CAG CAG GGG ACG GCC GCT CTG         198
Ser Gln Lys Gly Leu Asp Tyr Ala Ser Gln Gln Gly Thr Ala Ala Leu
 10              15                  20                      25

CAG AAG GAG CTG AAG AGG ATC AAG ATT CCT GAC TAC TCA GAC AGC TTT         246
Gln Lys Glu Leu Lys Arg Ile Lys Ile Pro Asp Tyr Ser Asp Ser Phe
                 30                  35                  40

AAG ATC AAG CAT CTT GGG AAG GGG CAT TAT AGC TTC TAC AGC ATG GAC         294
Lys Ile Lys His Leu Gly Lys Gly His Tyr Ser Phe Tyr Ser Met Asp
             45                  50                  55

ATC CGT GAA TTC CAG CTT CCC AGT TCC CAG ATA AGC ATG GTG CCC AAT         342
Ile Arg Glu Phe Gln Leu Pro Ser Ser Gln Ile Ser Met Val Pro Asn
         60                  65                  70

GTG GGC CTT AAG TTC TCC ATC AGC AAC GCC AAT ATC AAG ATC AGC GGG         390
Val Gly Leu Lys Phe Ser Ile Ser Asn Ala Asn Ile Lys Ile Ser Gly
     75                  80                  85

AAA TGG AAG GCA CAA AAG AGA TTC TTA AAA ATG AGC GGC AAT TTT GAC         438
Lys Trp Lys Ala Gln Lys Arg Phe Leu Lys Met Ser Gly Asn Phe Asp
 90                  95                 100                 105

CTG AGC ATA GAA GGC ATG TCC ATT TCG GCT GAT CTG AAG CTG GGC AGT         486
```

```
                                                      -continued

Leu Ser Ile Glu Gly Met Ser Ile Ser Ala Asp Leu Lys Leu Gly Ser
                110                 115                 120

AAC CCC ACG TCA GGC AAG CCC ACC ATC ACC TGC TCC AGC TGC AGC AGC        534
Asn Pro Thr Ser Gly Lys Pro Thr Ile Thr Cys Ser Ser Cys Ser Ser
            125                 130                 135

CAC ATC AAC AGT GTC CAC GTG CAC ATC TCA AAG AGC AAA GTC GGG TGG        582
His Ile Asn Ser Val His Val His Ile Ser Lys Ser Lys Val Gly Trp
            140                 145                 150

CTG ATC CAA CTC TTC CAC AAA AAA ATT GAG TCT GCG CTT CGA AAC AAG        630
Leu Ile Gln Leu Phe His Lys Lys Ile Glu Ser Ala Leu Arg Asn Lys
        155                 160                 165

ATG AAC AGC CAG GTC TGC GAG AAA GTG ACC AAT TCT GTA TCC TCC AAG        678
Met Asn Ser Gln Val Cys Glu Lys Val Thr Asn Ser Val Ser Ser Lys
170                 175                 180                 185

CTG CAA CCT TAT TTC CAG ACT CTG CCA GTA ATG ACC AAA ATA GAT TCT        726
Leu Gln Pro Tyr Phe Gln Thr Leu Pro Val Met Thr Lys Ile Asp Ser
                190                 195                 200

GTG GCT GGA ATC AAC TAT GGT CTG GTG GCA CCT CCA GCA ACC ACG GCT        774
Val Ala Gly Ile Asn Tyr Gly Leu Val Ala Pro Pro Ala Thr Thr Ala
                205                 210                 215

GAG ACC CTG GAT GTA CAG ATG AAG GGG GAG TTT TAC AGT GAG AAC CAC        822
Glu Thr Leu Asp Val Gln Met Lys Gly Glu Phe Tyr Ser Glu Asn His
                220                 225                 230

CAC AAT CCA CCT CCC TTT GCT CCA CCA GTG ATG GAG TTT CCC GCT GCC        870
His Asn Pro Pro Pro Phe Ala Pro Pro Val Met Glu Phe Pro Ala Ala
            235                 240                 245

CAT GAC CGC ATG GTA TAC CTG GGC CTC TCA GAC TAC TTC TTC AAC ACA        918
His Asp Arg Met Val Tyr Leu Gly Leu Ser Asp Tyr Phe Phe Asn Thr
250                 255                 260                 265

GCC GGG CTT GTA TAC CAA GAG GCT GGG GTC TTG AAG ATG ACC CTT AGA        966
Ala Gly Leu Val Tyr Gln Glu Ala Gly Val Leu Lys Met Thr Leu Arg
                270                 275                 280

GAT GAC ATG ATT CCA AAG GAG TCC AAA TTT CGA CTG ACA ACC AAG TTC       1014
Asp Asp Met Ile Pro Lys Glu Ser Lys Phe Arg Leu Thr Thr Lys Phe
                285                 290                 295

TTT GGA ACC TTC CTA CCT GAG GTG GCC AAG AAG TTT CCC AAC ATG AAG       1062
Phe Gly Thr Phe Leu Pro Glu Val Ala Lys Lys Phe Pro Asn Met Lys
            300                 305                 310

ATA CAG ATC CAT GTC TCA GCC TCC ACC CCG CCA CAC CTG TCT GTG CAG       1110
Ile Gln Ile His Val Ser Ala Ser Thr Pro Pro His Leu Ser Val Gln
        315                 320                 325

CCC ACC GGC CTT ACC TTC TAC CCT GCC GTG GAT GTC CAG GCC TTT GCC       1158
Pro Thr Gly Leu Thr Phe Tyr Pro Ala Val Asp Val Gln Ala Phe Ala
330                 335                 340                 345

GTC CTC CCC AAC TCC TCC CTG GCT TCC CTC TTC CTG ATT GGC ATG CAC       1206
Val Leu Pro Asn Ser Ser Leu Ala Ser Leu Phe Leu Ile Gly Met His
                350                 355                 360

ACA ACT GGT TCC ATG GAG GTC AGC GCC GAG TCC AAC AGG CTT GTT GGA       1254
Thr Thr Gly Ser Met Glu Val Ser Ala Glu Ser Asn Arg Leu Val Gly
            365                 370                 375

GAG CTC AAG CTG GAT AGG CTG CTC CTG GAA CTG AAG CAC TCA AAT ATT       1302
Glu Leu Lys Leu Asp Arg Leu Leu Leu Glu Leu Lys His Ser Asn Ile
        380                 385                 390

GGC CCC TTC CCG GTT GAA TTG CTG CAG GAT ATC ATG AAC TAC ATT GTA       1350
Gly Pro Phe Pro Val Glu Leu Leu Gln Asp Ile Met Asn Tyr Ile Val
        395                 400                 405

CCC ATT CTT GTG CTG CCC AGG GTT AAC GAG AAA CTA CAG AAA GGC TTC       1398
Pro Ile Leu Val Leu Pro Arg Val Asn Glu Lys Leu Gln Lys Gly Phe
410                 415                 420                 425
```

```
CCT CTC CCG ACG CCG GCC AGA GTC CAG CTC TAC AAC GTA GTG CTT CAG       1446
Pro Leu Pro Thr Pro Ala Arg Val Gln Leu Tyr Asn Val Val Leu Gln
            430                 435                 440

CCT CAC CAG AAC TTC CTG CTG TTC GGT GCA GAC GTT GTC TAT AAA           1491
Pro His Gln Asn Phe Leu Leu Phe Gly Ala Asp Val Val Tyr Lys
            445                 450                 455

TGAAGGCACC AGGGGTGCCG GGGGCTGTCA GCCGCACCTG TTCCTGATGG GCTGTGGGGC     1551

ACCGGCTGCC TTTCCCCAGG GAATCCTCTC CAGATCTTAA CCAAGAGCCC CTTGCAAACT     1611

TCTTCGACTC AGATTCAGAA ATGATCTAAA CACGAGGAAA CATTATTCAT TGAAAAGTG      1671

CATGGTGTGT ATTTTAGGGA TTATGAGCTT CTTTCAAGGG CTAAGGCTGC AGAGATATTT     1731

CCTCCAGGAA TCGTGTTTCA ATTGTAACCA AGAAATTTCC ATTTGTGCTT CATGAAAAAA     1791

AACTTCTGGT TTTTTTCATG TG                                              1813

(2) INFORMATION FOR SEQ ID NO:2:

(i) SEQUENCE CHARACTERISTICS:
        (A) LENGTH: 487 amino acids
        (B) TYPE: amino acid
        (D) TOPOLOGY: linear (ii) MOLECULE TYPE: protein (xi) SEQUENCE DESCRIPTION: SEQ ID NO:2:

Met Arg Glu Asn Met Ala Arg Gly Pro Cys Asn Ala Pro Arg Trp Val
-31 -30             -25                 -20

Ser Leu Met Val Leu Val Ala Ile Gly Thr Ala Val Thr Ala Ala Val
-15             -10                  -5                       1

Asn Pro Gly Val Val Arg Ile Ser Gln Lys Gly Leu Asp Tyr Ala
            5                  10                  15

Ser Gln Gln Gly Thr Ala Ala Leu Gln Lys Glu Leu Lys Arg Ile Lys
            20                  25                  30

Ile Pro Asp Tyr Ser Asp Ser Phe Lys Ile Lys His Leu Gly Lys Gly
        35                  40                  45

His Tyr Ser Phe Tyr Ser Met Asp Ile Arg Glu Phe Gln Leu Pro Ser
 50                  55                  60                  65

Ser Gln Ile Ser Met Val Pro Asn Val Gly Leu Lys Phe Ser Ile Ser
                70                  75                  80

Asn Ala Asn Ile Lys Ile Ser Gly Lys Trp Lys Ala Gln Lys Arg Phe
                85                  90                  95

Leu Lys Met Ser Gly Asn Phe Asp Leu Ser Ile Glu Gly Met Ser Ile
            100                 105                 110

Ser Ala Asp Leu Lys Leu Gly Ser Asn Pro Thr Ser Gly Lys Pro Thr
    115                 120                 125

Ile Thr Cys Ser Ser Cys Ser Ser His Ile Asn Ser Val His Val His
130                 135                 140                 145

Ile Ser Lys Ser Lys Val Gly Trp Leu Ile Gln Leu Phe His Lys Lys
                150                 155                 160

Ile Glu Ser Ala Leu Arg Asn Lys Met Asn Ser Gln Val Cys Glu Lys
            165                 170                 175

Val Thr Asn Ser Val Ser Ser Lys Leu Gln Pro Tyr Phe Gln Thr Leu
            180                 185                 190

Pro Val Met Thr Lys Ile Asp Ser Val Ala Gly Ile Asn Tyr Gly Leu
        195                 200                 205

Val Ala Pro Pro Ala Thr Thr Ala Glu Thr Leu Asp Val Gln Met Lys
210                 215                 220                 225
```

```
Gly Glu Phe Tyr Ser Glu Asn His His Asn Pro Pro Pro Phe Ala Pro
                230             235             240

Pro Val Met Glu Phe Pro Ala Ala His Asp Arg Met Val Tyr Leu Gly
            245             250             255

Leu Ser Asp Tyr Phe Phe Asn Thr Ala Gly Leu Val Tyr Gln Glu Ala
            260             265             270

Gly Val Leu Lys Met Thr Leu Arg Asp Asp Met Ile Pro Lys Glu Ser
    275             280             285

Lys Phe Arg Leu Thr Thr Lys Phe Phe Gly Thr Phe Leu Pro Glu Val
290             295             300             305

Ala Lys Lys Phe Pro Asn Met Lys Ile Gln Ile His Val Ser Ala Ser
            310             315             320

Thr Pro Pro His Leu Ser Val Gln Pro Thr Gly Leu Thr Phe Tyr Pro
            325             330             335

Ala Val Asp Val Gln Ala Phe Ala Val Leu Pro Asn Ser Ser Leu Ala
            340             345             350

Ser Leu Phe Leu Ile Gly Met His Thr Thr Gly Ser Met Glu Val Ser
    355             360             365

Ala Glu Ser Asn Arg Leu Val Gly Glu Leu Lys Leu Asp Arg Leu Leu
370             375             380             385

Leu Glu Leu Lys His Ser Asn Ile Gly Pro Phe Pro Val Glu Leu Leu
            390             395             400

Gln Asp Ile Met Asn Tyr Ile Val Pro Ile Leu Val Leu Pro Arg Val
            405             410             415

Asn Glu Lys Leu Gln Lys Gly Phe Pro Leu Pro Thr Pro Ala Arg Val
            420             425             430

Gln Leu Tyr Asn Val Val Leu Gln Pro His Gln Asn Phe Leu Leu Phe
    435             440             445

Gly Ala Asp Val Val Tyr Lys
450             455
```

THERAPEUTIC USES OF N-TERMINAL BPI PROTEIN PRODUCTS IN ANCA-POSITIVE PATIENTS

This is a Continuation of U.S. application Ser. No. 08/742,985, filed Nov. 1, 1996, now abandoned.

BACKGROUND OF THE INVENTION

The present invention relates generally to novel improved methods of treating subjects that have BPI-reactive anti-neutrophil cytoplasmic antibodies by administering N-terminal bactericidal/permeability-increasing protein (BPI) protein products.

Anti-neutrophil cytoplasmic antibodies (ANCA) have been recognized as a class of autoantibodies that react with the cytoplasmic constituents of neutrophils and monocytes. ANCA are detected by indirect immunofluorescence (IIF) on ethanol-fixed neutrophils, and produce at least three distinct immunofluorescence patterns: cANCA (cytoplasmic, or 'classic' pattern), pANCA (perinuclear to nuclear pattern) or aANCA (atypical, with a peculiar "snow drift pattern"). [Kallenberg et al., Am. J. Med., 93:675–682 (1992).] The presence of ANCA has been associated with various idiopathic systemic vasculitis disorders (i.e., inflammation of and damage to the blood vessels) and with other inflammatory disorders, and can be diagnostic of certain vasculitides. These vasculitides are sometimes called ANCA-associated vasculitides (AAV). A pathophysiologic role for ANCA in vasculitides has been proposed but remains to be definitively established. [Kallenberg et al., Clin. Exp. Immunol., 100:1–3 (1995).]

The antigen primarily recognized by c-ANCA proved to be a 29kd serine protease from myeloid azurophilic granules known as proteinase 3 (PR-3). The presence of anti-PR3 is highly correlated to cANCA and is specific for idiopathic vasculitides such as Wegener's granulomatosis (WG), microscopic polyarteritis (MPA) and the renal limited pauci-immune necrotizing and crescentic glomerulonephritis (NCGN). [Kallenberg, 1995, supra.]

One of the antigens recognized by p-ANCA is myeloperoxidase (MPO), another constituent of azurophilic granules. However, only a minority of p-ANCA-positive sera reacts with MPO. Anti-MPO antibodies have been found to be specific for systemic vasculitis and idiopathic crescentic glomerulonephritis. Anti-MPO antibodies are also found in patients with anti-glomerular basement membrane disease and in some sera of patients with systemic lupus erythematosus (SLE). The presence of p-ANCA has also been described in sera from patients with a wide range of different disorders such as colitides (including ulcerative colitis, inflammatory bowel disease, Crohn's disease and collagenous colitis), autoimmune liver diseases (including autoimmune chronic active hepatitis, primary sclerosing cholangitis and primary biliary cirrhosis) and rheumatoid arthritis. [Kallenberg, 1992, supra.] These latter p-ANCA generally do not react with MPO, and their antigenic specificities are largely unknown. Some antibodies to leukocyte elastase and lactoferrin have also been described that produce a p-ANCA pattern by IIF. Antibodies to elastase occur occasionally in sera from patients with vasculitis or drug-induced systemic autoimmune disease. Lactoferrin antibodies have been seen in a few patients with vasculitis, primary sclerosing cholangitis and ulcerative colitis, and in a minority of patients with rheumatoid arthritis. Their diagnostic value has not been established yet.

BPI has been identified as another ANCA antigen. Falk et al., Third Int'l Workshop on ANCA, Am J. Kidney Dis., 18:197 (abst. 6) (1991), reported that 11 of 51 cANCA-positive samples recognized a 57-kD antimicrobial cationic protein (CAP57), which was later identified as BPI by N-terminal amino acid sequence homology and immunoreactivity. This CAP57-specific cANCA staining was blocked by anti-CAP57 monoclonal antibodies but not by anti-MPO or anti-PR3 monoclonal antibodies. No clinical details of the patients, with respect to whether or not they had vasculitis, and if so, the distribution, were reported in this abstract.

Zhao et al., Clin. Exp. Immunol., 99:49–56 (1995) also reported the identification of BPI-reactive ANCA in serum samples from patients with suspected vasculitis. Of 100 historical serum samples that were double-negative for PR3 and MPO specificity by ELISA, 45% were reactive with purified BPI. Of 400 newly obtained samples sent for routine ANCA testing, 11% had BPI specificity, suggesting that BPI is an important ANCA antigen. The PR3 and MPO specificities in these 400 new samples were 10/400 and 14/400 respectively. Zhao et al. conjectured that these human autoantibodies against BPI might block the bactericidal and LPS-neutralizing activities of BPI, allowing these non-neutralized products to directly cause vascular damage and initiate vasculitis.

BPI is a protein isolated from the granules of mammalian polymorphonuclear leukocytes (PMNs or neutrophils), which are blood cells essential in the defense against invading microorganisms. Human BPI protein has been isolated from PMNs by acid extraction combined with either ion exchange chromatography [Elsbach, J. Biol. Chem., 254:11000 (1979)] or E. coli affinity chromatography [Weiss, et al., Blood, 69:652 (1987)]. BPI obtained in such a manner is referred to herein as natural BPI and has been shown to have potent bactericidal activity against a broad spectrum of gram-negative bacteria. The molecular weight of human BPI is approximately 55,000 daltons (55 kD). The amino acid sequence of the entire human BPI protein and the nucleic acid sequence of DNA encoding the protein have been reported in FIG. 1 of Gray et al., J. Biol. Chem., 264:9505 (1989), incorporated herein by reference. The Gray et al. amino acid sequence is set out in SEQ ID NO: 1 hereto. U.S. Pat. No. 5,198,541 discloses recombinant genes encoding and methods for expression of BPI proteins, including BPI holoprotein and fragments of BPI.

BPI is a strongly cationic protein. The N-terminal half of BPI accounts for the high net positive charge; the C-terminal half of the molecule has a net charge of −3. [Elsbach and Weiss (1981), supra.] A proteolytic N-terminal fragment of BPI having a molecular weight of about 25 kD possesses essentially all the anti-bacterial efficacy of the naturally-derived 55 kD human BPI holoprotein. [Ooi et al., J. Bio. Chem., 262: 14891–14894 (1987)]. In contrast to the N-terminal portion, the C-terminal region of the isolated human BPI protein displays only slightly detectable anti-bacterial activity against gram-negative organisms. [Ooi et al., J. Exp. Med., 174:649 (1991).] An N-terminal BPI fragment of approximately 23 kD, referred to as "rBPI$_{23}$," has been produced by recombinant means and also retains anti-bacterial activity against gram-negative organisms. [Gazzano-Santoro et al., Infect. Immun. 60:4754–4761 (1992).] An N-terminal analog of BPI, rBPI$_{21}$, has been produced as described in Horwitz et al., Protein Expression Purification, 8:28–40 (1996).

The bactericidal effect of BPI has been reported to be highly specific to gram-negative species, e.g., in Elsbach and Weiss, Inflammation: Basic Principles and Clinical Correlates, eds. Gallin et al., Chapter 30, Raven Press, Ltd. (1992). The precise mechanism by which BPI kills gram-negative bacteria is not yet completely elucidated, but it is believed that BPI must first bind to the surface of the bacteria through electrostatic and hydrophobic interactions between the cationic BPI protein and negatively charged sites on LPS. In susceptible gram-negative bacteria, BPI binding is thought to disrupt LPS structure, leading to activation of bacterial enzymes that degrade phospholipids and peptidoglycans, altering the permeability of the cell's outer membrane, and initiating events that ultimately lead to cell death. [Elsbach and Weiss (1992), supra]. LPS has been referred to as "endotoxin" because of the potent inflammatory response that it stimulates, i.e., the release of mediators by host inflammatory cells which may ultimately result in irreversible endotoxic shock. BPI binds to lipid A, reported to be the most toxic and most biologically active component of LPS.

BPI protein products, as discussed infra, have a wide variety of beneficial activities in addition to their gram-negative bactericidal activities. The observation of antibodies reactive against BPI among ANCA-positive subjects suggests that these antibodies may interfere with the activities of BPI. A need therefore exists for improved methods of treating subjects that have BPI-reactive ANCA with BPI protein products.

SUMMARY OF THE INVENTION

The present invention provides novel improved methods of treating subjects that have non-N-terminal-BPI-reactive antibodies by administering N-terminal bactericidal/permeability-increasing (BPI) protein products. The invention is based on the discovery that BPI-reactive autoantibodies bind to BPI holoprotein but have very little reactivity with N-terminal BPI protein products. Interference with the beneficial activities of endogenous BPI or exogenous BPI protein products can therefore be avoided by administering N-terminal BPI protein products.

It is contemplated that these improved methods will be useful when the N-terminal BPI protein product is being administered for any of the indications presently known for BPI protein products. For example, the N-terminal BPI protein product may be administered to a human subject to ameliorate adverse effects associated with endotoxin in circulation, meningococcemia, hemorrhagic trauma, burn trauma, ischemia/reperfusion injury, or liver resection injury. A N-terminal BPI protein product may also be administered for the treatment of gram-negative bacterial infection, gram-positive bacterial or mycoplasmal infection, fungal infection, protozoal infection, chlamydial infection, mycobacterial infection, chronic inflammatory diseases, including rheumatoid and reactive arthritis, or to enhance the effectiveness of antibiotic activity, or to inhibit angiogenesis or to promote fibrinolysis.

Presently preferred N-terminal BPI protein products include amino-terminal fragments of BPI protein having a molecular weight of about 20 kD to 25 kD, rBPI$_{23}$ or a dimeric form thereof, and rBPI$_{21}$.

It is contemplated that the administration of BPI protein products, especially N-terminal BPI protein products, according to all aspects of the present invention may be accompanied by the concurrent administration of other therapeutic agents such as antimicrobial agents, including antibiotics and anti-fungal agents.

Numerous additional aspects and advantages of the invention will become apparent to those skilled in the art upon consideration of the following detailed description of the invention which describes presently preferred embodiments thereof.

DETAILED DESCRIPTION OF THE INVENTION

The present invention provides improved methods of treating subjects that have non-N-terminal-BPI-reactive antibodies, the presence of which may interfere with the activities of BPI protein products in these subjects, by the administration of N-terminal BPI protein products. The invention is based on the discovery that BPI-reactive autoantibodies bind to BPI holoprotein but have very little reactivity with N-terminal BPI protein products; the ANCA-recognized epitopes thus appear to reside predominantly outside the N-terminal 193 amino acids of BPI.

BPI protein products are known to have a variety of beneficial activities. BPI protein products are known to be bactericidal for gram-negative bacteria, as described in U.S. Pat. Nos. 5,198,541 and 5,523,288, both of which are incorporated herein by reference. BPI protein products are also known to enhance the effectiveness of antibiotic therapy in gram-negative bacterial infections, as described in U.S. Pat. No. 5,523,288, which is incorporated herein by reference. BPI protein products are also known to be bactericidal for gram-positive bacteria and mycoplasma, and to enhance the effectiveness of antibiotics in gram-positive bacterial infections, as described in co-owned U.S. Pat. No. 5,846,154 filed Jan. 13, 1995, which is in turn a continuation-in-part of U.S. application Ser. No. 08/274,299 filed Jul. 11, 1994, now abandoned, and corresponding International Publication No. WO 95/08344 (PCT/US94/11225), all of which are incorporated herein by reference. BPI protein products are further known to exhibit anti-fungal activity, and to enhance the activity of other anti-fungal agents, as described in co-owned U.S. Pat. No. 5,627,153 filed Jan. 13, 1995, which is in turn a continuation-in-part of U.S. application Ser. No. 08/273,540 filed Jul. 11, 1994, now abandoned, and corresponding International Publication No. WO 95/19179 (PCT/US95/00498), and further as described for anti-fungal peptides in co-owned, U.S. Pat. No. 5,858,974 filed Mar. 21, 1996, which is in turn a continuation-in-part of U.S. application Ser. No. 08/504,841 filed Jul. 20, 1994, now abandoned, and corresponding International Publication No. WO 96/08509 (PCT/US95/09262) and PCT Application No. PCT/US96/03845, all of which are incorporated herein by reference. BPI protein products are further known to exhibit anti-protozoan activity, as described in co-owned U.S. Pat. No. 5,646,114 filed Jul. 11, 1994 and corresponding International Publication No. WO 96/101647 (PCT/US95/08624), all of which are incorporated herein by reference. BPI protein products are known to exhibit anti-chlamydial activity, as described in co-owned U.S Pat. No. 5,888,973 filed Aug. 9, 1996, all of which are incorporated herein by reference. Finally, BPI protein products are known to exhibit anti-mycobacterial activity, as described in co-owned U.S. Pat. No. 6,214,789 filed Apr. 1, 1996, which is in turn a continuation of U.S. application Ser. No. 08/285,803 filed Aug. 14, 1994, now abandoned, which is in turn a continuation-in-part of U.S. application Ser. No. 08/031,145 filed Mar. 12, 1993, now abandoned, and corresponding International Publication No. WO94/20129 (PCT/US94/02463), all of which are incorporated herein by reference.

The effects of BPI protein products in humans with endotoxin in circulation, including effects on TNF, IL-6 and endotoxin are described in co-owned U.S. Pat. No. 5,753,620, filed Jan. 24, 1995, which in turn is a continuation-in-part application of U.S. Pat. No. 5,643,875 which in turn is a continuation-in-part application of U.S. Ser. No. 08/188,221, filed Jan. 24, 1994, now abandoned, and corresponding International Publication No. WO 95/19784 (PCT/US95/01151), all of which are incorporated herein by reference.

BPI protein products are also known to be useful for treatment of specific disease conditions, such as meningococcemia in humans (as described in co-owned U.S. application Ser. No. 08/644,287 filed May 10, 1996, now abandoned, incorporated herein by reference), hemorrhagic trauma in humans, (as described in co-owned U.S. application Ser. No. 08/652,292 filed May 23, 1996, now abandoned, incorporated herein by reference), burn injury (as described in U.S. Pat. No. 5,494,896 and corresponding International Publication No. WO 96/30037 (PCT/US96/02349), both of which are incorporated herein by reference), ischemia/reperfusion injury (as described in co-owned U.S. Pat. No. 5,578,568 filed Apr. 22, 1994, incorporated herein by reference), and liver resection (as described in co-owned U.S. application Ser. No. 08/582,230 filed Jan. 3, 1996, now abandoned, which is in turn a continuation of U.S. application Ser. No. 08/318,357 filed Oct. 5, 1994, now abandoned, which is in turn a continuation-in-part of U.S. application Ser. No. 08/132,510 filed Oct. 5, 1993, now abandoned, and corresponding International Publication No. WO 95/10297 (PCT/US94/11404), all of which are incorporated herein by reference).

BPI protein products are also known to neutralize the anti-coagulant activity of exogenous heparin, as described in U.S. Pat. No. 5,348,942, incorporated herein by reference, as well as to be useful for treating chronic inflammatory diseases such as rheumatoid and reactive arthritis and for inhibiting angiogenesis and for treating angiogenesis-associated disorders including malignant tumors, ocular retinopathy and endometriosis, as described in co-owned U.S. Pat. No. 5,639,727 filed Mar. 31, 1995, which is in turn a continuation of U.S. application Ser. No. 08/093,202, filed Jul. 15, 1993, now abandoned, which is in turn a continuation-in-part of U.S. Pat. No. 5,348,942, filed Mar. 12, 1993, all of which are incorporated herein by reference.

BPI protein products are also known for use in antithrombotic methods, as described in co-owned U.S. Pat. No. 5,741,779 filed May 10, 1996, incorporated herein by reference.

As used herein, "BPI protein product" includes naturally and recombinantly produced BPI protein; natural, synthetic, and recombinant biologically active polypeptide fragments of BPI protein; biologically active polypeptide variants of BPI protein or fragments thereof, including hybrid fusion proteins and dimers; biologically active polypeptide analogs of BPI protein or fragments or variants thereof, including cysteine-substituted analogs; and BPI-derived peptides. The BPI protein products administered according to this invention may be generated and/or isolated by any means known in the art. U.S. Pat. No. 5,198,541, the disclosure of which is incorporated herein by reference, discloses recombinant genes encoding, and methods for expression of, BPI proteins including recombinant BPI holoprotein, referred to as rBPI and recombinant fragments of BPI. U.S. Pat. No. 5,439,807 and corresponding International Publication No. WO 93/23540 (PCT/US93/04752), which are all incorporated herein by reference, disclose novel methods for the purification of recombinant BPI protein products expressed in and secreted from genetically transformed mammalian host cells in culture and discloses how one may produce large quantities of recombinant BPI products suitable for incorporation into stable, homogeneous pharmaceutical preparations.

Biologically active fragments of BPI (BPI fragments) include biologically active molecules that have the same or similar amino acid sequence as a natural human BPI holoprotein, except that the fragment molecule lacks amino-terminal amino acids, internal amino acids, and/or carboxy-terminal amino acids of the holoprotein. Nonlimiting examples of such fragments include an N-terminal fragment of natural human BPI of approximately 25 kD, described in Ooi et al., *J. Exp. Med.*, 174:649 (1991), and the recombinant expression product of DNA encoding N-terminal amino acids from 1 to about 193 to 199 of natural human BPI, described in Gazzano-Santoro et al., *Infect. Immun.* 60:4754–4761 (1992), and referred to as $rBPI_{23}$. In that publication, an expression vector was used as a source of DNA encoding a recombinant expression product ($rBPI_{23}$) having the 31-residue signal sequence and the first 199 amino acids of the N-terminus of the mature human BPI, as set out in FIG. 1 of Gray et al., supra, except that valine at position 151 is specified by GTG rather than GTC and residue 185 is glutamic acid (specified by GAG) rather than lysine (specified by AAG). Recombinant holoprotein (rBPI) has also been produced having the sequence set out in FIG. 1 of Gray et al., supra, with the exceptions noted for $rBPI_{23}$ and with the exception that residue 417 is alanine (specified by GCT) rather than valine (specified by GTT). Other examples include dimeric forms of BPI fragments, as described in U.S. Pat. No. 5,447,913 and corresponding International Publication No. WO 95/24209 (PCT/US95/03125), all of which are incorporated herein by reference.

Biologically active variants of BPI (BPI variants) include but are not limited to recombinant hybrid fusion proteins, comprising BPI holoprotein or biologically active fragment thereof and at least a portion of at least one other polypeptide, and dimeric forms of BPI variants. Examples of such hybrid fusion proteins and dimeric forms are described in co-owned U.S. application Ser. No. 07/885,911 filed May 19, 1992, now abandoned, U.S. Pat. No. 5,643,570 and corresponding International Publication No. WO 93/23434 (PCT/US93/04754), which are all incorporated herein by reference and include hybrid fusion proteins comprising, at the amino-terminal end, a BPI protein or a biologically active fragment thereof and, at the carboxy-terminal end, at least one constant domain of an immunoglobulin heavy chain or allelic variant thereof.

Biologically active analogs of BPI (BPI analogs) include but are not limited to BPI protein products wherein one or more amino acid residues have been replaced by a different amino acid. For example, U.S. Pat. No. 5,420,019 and corresponding International Publication No. WO 94/18323 (PCT/US94/01235), all of which are incorporated herein by reference, discloses polypeptide analogs of BPI and BPI fragments wherein a cysteine residue is replaced by a different amino acid. A stable BPI protein product described by this application is the expression product of DNA encoding from amino acid 1 to approximately 193 or 199 of the N-terminal amino acids of BPI holoprotein, but wherein the cysteine at residue number 132 is substituted with alanine and is designated $rBPI_{21}\Delta cys$ or $rBPI_{21}$. Production of this N-terminal analog of BPI, $rBPI_{21}$, has been described in Horwitz et al., *Protein Expression Purification*, 8:28–40 (1996). Other examples include dimeric forms of BPI analogs; e.g. U.S. Pat. No. 5,447,913 and corresponding International Publication No. WO 95/24209 (PCT/US95/03125); all of which are incorporated herein by reference.

Other BPI protein products useful according to the methods of the invention are peptides derived from or based on BPI produced by recombinant or synthetic means (BPI-derived peptides), such as those described in International Publication No. WO 95/19372 (PCT/US94/10427), which corresponds to U.S. Pat. No. 5,652,332, and International Publication No. WO94/20532 (PCT/US94/02465), which corresponds to U.S. Pat. No. 5,733,872, filed Mar. 11, 1994, which is a continuation-in-part of U.S. application Ser. No. 08/183,222, filed Jan. 14, 1994, now abandoned, which is a continuation-in-part of U.S. application Ser. No. 08/093,202 filed Jul. 15, 1993, now abandoned (corresponding to International Publication No. WO 94/20128 (PCT/US94/02401)), which is a continuation-in-part of U.S. Pat. No. 5,348,942 filed Mar. 12, 1993, the disclosures of all of which are incorporated herein by reference.

As used herein, an "N-terminal BPI protein product" as differentiated from a "BPI protein product" includes natural, synthetic, and recombinant biologically active N-terminal polypeptide fragments of BPI protein having a molecular weight of about 25 kd or less; biologically active polypeptide analogs of these N-terminal BPI fragments, including cysteine-substituted analogs; biologically active polypeptide variants comprising such N-terminal BPI fragments or analogs thereof, including hybrid fusion proteins and dimers; and peptides derived from or based on N-terminal BPI protein having a molecular weight of about 25 kd or less (BPI-derived peptides).

Presently preferred BPI protein products include recombinantly-produced N-terminal fragments of BPI, especially those having a molecular weight of approximately between 20 to 25 kD such as $rBPI_{21}$ or $rBPI_{23}$, or dimeric forms of these N-terminal fragments (e.g., $rBPI_{42}$ dimer). Preferred N-terminal dimeric products include dimeric BPI protein products wherein the monomers are N-terminal BPI fragments having the N-terminal residues from about 1 to 175 to about 1 to 199 of BPI holoprotein. A particularly preferred N-terminal dimeric product is the dimeric form of the BPI fragment having N-terminal residues 1 through 193, designated $rBPI_{42}$ dimer. Additionally, preferred N-terminal BPI protein products include rBPI and BPI-derived peptides.

The administration of N-terminal BPI protein products is preferably accomplished with a pharmaceutical composition comprising an N-terminal BPI protein product and a pharmaceutically acceptable diluent, adjuvant, or carrier. The N-terminal BPI protein product may be administered without or in conjunction with known surfactants, other chemotherapeutic agents or additional known anti-chlamydial agents. A stable pharmaceutical composition containing BPI protein products (e.g., $rBPI_{23}$) comprises the BPI protein product at a concentration of 1 mg/ml in citrate buffered saline (5 or 20 mM citrate, 150 mM NaCl, pH 5.0) comprising 0.1% by weight of poloxamer 188 (Pluronic F-68, BASF Wyandotte, Parsippany, N.J.) and 0.002% by weight of polysorbate 80 (Tween 80, ICI Americas Inc., Wilmington, Del.). Another stable pharmaceutical composition containing BPI protein products (e.g., $rBPI_{21}$) comprises the BPI protein product at a concentration of 2 mg/ml in 5 mM citrate, 150 mM NaCl, 0.2% poloxamer 188 and 0.002% polysorbate 80. Such preferred combinations are described in U.S. Pat. No. 5,488,034 and corresponding International Publication No. WO 94/17819 (PCT/US94/01239), the disclosures of all of which are incorporated herein by reference. As described in U.S. application Ser. No. 08/586,133 filed Jan. 12, 1996, now U.S. Pat. No. 5,912,228 which is in turn a continuation-in-part of U.S. application Ser. No. 08/530,599 filed Sep. 19, 1995, now abandoned, which is in turn a continuation-in-part of U.S. Pat. No. 5,868,374 filed Jan. 13, 1995, and corresponding International Publication No. WO96/21436 (PCT/US96/01095), all of which are incorporated herein by reference, other poloxamer formulations of BPI protein products with enhanced activity may be utilized.

Therapeutic compositions comprising N-terminal BPI protein product may be administered systemically or topically. Systemic routes of administration include oral, intravenous, intramuscular or subcutaneous injection (including into a depot for long-term release), intraocular and retrobulbar, intrathecal, intraperitoneal (e.g. by intraperitoneal lavage), intrapulmonary (using powdered drug, or an aerosolized or nebulized drug solution), or transdermal.

When given parenterally, N-terminal BPI protein product compositions are generally injected in doses ranging from 1 μg/kg to 100 mg/kg per day, preferably at doses ranging from 0.1 mg/kg to 20 mg/kg per day, more preferably at doses ranging from 1 to 20 mg/kg/day and most preferably at doses ranging from 2 to 10 mg/kg/day. The treatment may continue by continuous infusion or intermittent injection or infusion, at the same, reduced or increased dose per day for, e.g., 1 to 3 days, and additionally as determined by the treating physician. When administered intravenously, N-terminal BPI protein products are preferably administered by an initial brief infusion followed by a continuous infusion. The preferred intravenous regimen is a 1 to 20 mg/kg brief intravenous infusion of N-terminal BPI protein product followed by a continuous intravenous infusion at a dose of 1 to 20 mg/kg/day, continuing for up to one week. A particularly preferred intravenous dosing regimen is a 1 to 4 mg/kg initial brief intravenous infusion followed by a continuous intravenous infusion at a dose of 1 to 4 mg/kg/day, continuing for up to 72 hours.

Topical routes include administration in the form of salves, creams, jellies, ophthalmic drops or ointments (as described in co-owned U.S. application Ser. No. 08/557,289 (now abandoned) and U.S. Pat. No. 5,686,414, both filed Nov. 14, 1995), ear drops, suppositories, irrigation fluids (for, e.g., irrigation of wounds) or medicated shampoos. For example, for topical administration in drop form, about 10 to 200 μL of an N-terminal BPI protein product composition may be applied one or more times per day as determined by the treating physician.

Those skilled in the art can readily optimize effective dosages and administration regimens for therapeutic compositions comprising N-terminal BPI protein product, as determined by good medical practice and the clinical condition of the individual patient.

"Concurrent administration" as used herein includes administration of the agents together, or before or after each other. The BPI protein products and second agent(s) may be administered by different routes. For example, the BPI protein product may be administered intravenously while the second agent(s) is(are) administered intramuscularly, intravenously, subcutaneously, orally or intraperitoneally. Alternatively, the BPI protein product may be administered intraperitoneally while the second agent(s) is (are) administered intraperitoneally or intravenously, or the BPI protein product may be administered in an aerosolized or nebulized form while the second agent(s) are administered, e.g., intravenously. The BPI protein product and second agent(s) may be both administered intravenously. The BPI protein product and second agent(s) may be given sequentially in the same intravenous line, after an intermediate flush, or may be given in different intravenous lines. The BPI protein product and second agent(s) may be administered simultaneously or sequentially, as long as they are given in a manner sufficient to allow all agents to achieve effective concentrations at the site of infection.

Other aspects and advantages of the present invention will be understood upon consideration of the following illustrative examples. Example 1 addresses the determination of BPI reactivity in the sera of ANCA-positive patients.

EXAMPLE 1

Measurement of BPI Antibody Titers in Sera of ANCA-Positive Patients

The presence of anti-BPI antibodies was determined in sera from 112 patients with confirmed ANCA-associated vasculitides (Wegener's granulomatosis, microscopic polyangiitis and Chung-Strauss syndrome), focusing on "double-negative" sera. Results are set forth in Table 1 below.

TABLE 1

BPI-ANCA in ANCA-associated vasculitides according to the main target antigens

|  | Wegener's granulomatosis | | Microscopic polyangiitis | | Chung-Strauss syndrome | |
| --- | --- | --- | --- | --- | --- | --- |
|  | +/Σ | % | +/Σ | % | +/Σ | % |
| IIF/ANCA(+) | 34/45 | 78 | 13/22 | 59 | 30/45 | 67 |
| PR3(+) | 18/35 | 51* | 0/13 | 0 | 3/30 | 10 |
| MPO(+) | 0/35 | 0 | 8/13 | 62 | 5/30 | 17 |
| BPI(+) | 3†/35 | 9 | 1‡/13 | 8 | 0/30 | 0 |
| Unknown | 14/35 | 40 | 4/13 | 31 | 22/30 | 73 |
| IIF/ANCA(−) | 10/45 | 22 | 9/22 | 41 | 15/45 | 33 |
| BPI(+) | 0/10 | 0 | 0/9 | 0 | 3/15 | 20 |

*Low due to selection method.
†No proteinase 3 (PR3) specificity.
‡No myeloperoxidase (MPO) specificity.

A considerable amount of sera that was ANCA negative by IIF proved to be BPI-reactive by ELISA, suggesting that screening for BPI reactivity by ELISA provides increased sensitivity compared to conventional indirect immunofluorescence techniques.

The sera of 102 patients with inflammatory bowel disease and primary sclerosing cholangitis were also evaluated for reactivity to BPI by ELISA. For comparison, 182 disease controls and 140 healthy blood donors were screened by means by ELISA using recombinant BPI (rBPI) as antigen (rBPI-ANCA-ELISA). Western blotting techniques were used to confirm the antigen recognized by these BPI-ANCA.

BPI-ANCA were detected in 36% of primary sclerosing cholangitis patients (44% of ANCA+patients), 26% of ulcerative colitis patients (29% of ANCA+) and 21% of Crohn's disease patients (24% of ANCA+), compared to less than 10% of ANCA-associated vasculitides (AAV) patients and disease controls.

In the group of AAV patients (selected according to ANCA status), 32% (36/112) were cANCA positive, 33.1% (37/112) pANCA positive, and 35% (39/112) were ANCA negative (table 1). In Wegener's granulomatosis, only 7% (3/45), in microscopic polyangiitis only 5% (1/22), and in Chung-Strauss syndrome only 7% (3/45) of sera were BPI-ANCA positive. All 3 BPI-ANCA-positive Chung-Strauss syndrome patients belonged to the ANCA negative subset.

In inflammatory bowel disease and primary sclerosing cholangitis, 52% (53/102) of patients were pANCA and 12.8% (13/102 were aANCA positive, while 35.2% (36/102) were ANCA negative (table 2). BPI-ANCA were present in 33% of ANCA-positive (by IIF) inflammatory bowel disease and primary sclerosing cholangitis patients. Primary sclerosing cholangitis showed the highest proportions of BPI-ANCA positively (44%), followed by ulcerative colitis (29%) and Crohn's disease (24%). In contrast to AAV, where BPI-ANCA do not further specify ANCA-positive and ANCA-negative sera, BPI-ANCA in inflammatory bowel disease and primary sclerosing cholangitis were also detected in 18% (primary sclerosing cholangitis, Crohn's disease) and 14% (ulcerative colitis) of "ANCA-negative" patients as assessed by IIF.

In the disease controls, none of the patients were cANCA positive, 31% (56/182) were pANCA and 10% (18/182) aANCA positive, while 59% (107/182) were ANCA negative. The sera from these patients did not show BPI-ANCA in significant numbers, either in the non-ANCA-associated vasculitis group (represented by 'classic' polyarteritis nodosa, Kawasaki's disease, Takayasu's and temporal arteritis, and Henoch-Schoeniein purpura) or in collagen vascular diseases (systemic lupus erythematosus [SLE], systemic sclerosis, polymyositis) and rheumatoid arthritis.

All 140 healthy blood donors were ANCA negative. Only one healthy donor was positive for BPI-ANCA as demonstrated by ELISA, exhibited no apparent clinical disease.

The frequency of BPI-ANCA in the diseases studied is shown according to their ANCA status (by IIF) in Table 2 below.

TABLE 2

|  | BPI-ANCA +* | | | | | |
| --- | --- | --- | --- | --- | --- | --- |
|  | (Total) | | (ANCA +)† | | (ANCA −)† | |
| Diseases | n/Σ | (%) | n/Σ | (%) | n/Σ | (%) |
| ANCA-associated vasculituudes |  |  |  |  |  |  |
| Wegener's granulomatosis | 3/45 | 7% | <10%‡ | | | |
| Chung-Strauss syndrome | 3/45 | 7% | | | | |
| Microscopic polyangiitis | 1/22 | 5% | | | | |
| Chronic inflammatory bowel disease |  |  |  |  |  |  |
| Crohn's Disease | 10/44 | 23% | 5/20 | 25% | 5/24 | 21% |
| Ulcerative colitis | 20/54 | 37% | 15/39 | 38% | 5/15 | 33% |
| Primary sclerosing cholangitis | 13/36 | 36% | 11/25 | 44% | 2/11 | 18% |
| Disease controls |  |  |  |  |  |  |
| "Classical" polyarteritis nodosa | 0/14 | 0% |  |  |  |  |
| Kawasaki's Disease | 0/9 | 0% |  |  |  |  |
| Takayasu's Disease | 1/10 | 10% | <10%‡ | | | |
| Henoch-Schoenleim purpura | 1/16 | 6% |  |  |  |  |
| Temporal arteritis | 4/42 | 9% |  |  |  |  |
| Systemic lupus erythematosus | 2/28 | 7% | <7%‡ | | | |
| Systemic sclerosis | 0/13 | 0% |  |  |  |  |
| Polymyositis | 0/12 | 0% |  |  |  |  |
| Rheumatoid arthritis | 3/38 | 8% | <10%‡ | | | |
| Healthy controls | 1/140 | <0.1% | <0.1%‡ | | | |

*ELISA.
†Indirect immunofluorescence test screening.
‡ConsideRed not significant.

In inflammatory bowel diseases (33.8%) and autoimmune liver disease (42.9%), anti-BPI antibodies are of major importance, appearing in more than one third of ANCA positive patients. BPI can thus be used as a recognized seromarker for a distinct disease entity.

To narrow the reactivity of the anti-BPI antibodies to a particular portion of the BPI molecule, all 60 of the samples that were reactive with BPI holoprotein (as shown in Table 2) were also screened with an N-terminal BPI protein product, $rBPI_{21}$. Of these 60 samples, only 6 (12%) appeared to be reactive with $rBPI_{21}$. A large amount of nonspecific binding was observed generally when rBPI$_{21}$ was used as the antigen. This low level of reactivity with N-terminal BPI protein product indicated that the ANCA-recognized epitopes appear to reside predominantly outside the N-terminal 193 amino acids of BPI.

It has also been determined that BPI-reactive antibodies in cystic fibrosis patients are not reactive with the N-terminal BPI protein product rBPI$_{21}$. See co-owned U.S. application Ser. No. 08/742,986 filed concurrently herewith, now abandoned, incorporated herein by reference.

Numerous modifications and variations of the above-described invention are expected to occur to those of skill in the art. Accordingly, only such limitations as appear in the appended claims should be placed thereon.

---

What is claimed is:

1. In a method of treating a subject with a bactericidal/permeability-increasing (BPI) protein product, the improvement comprising administering an N-terminal BPI protein product to a subject having non-N-terminal-BPI-reactive antibodies.

2. The method of claim 1 wherein the N-terminal BPI protein product is being administered to a human subject to ameliorate adverse effects associated with endotoxin in circulation.

3. The method of claim 1 wherein the N-terminal BPI protein product is being administered to a human subject to ameliorate adverse effects associated with meningococcemia.

4. The method of claim 1 wherein the N-terminal BPI protein product is being administered to a human subject to ameliorate adverse effects associated with hemorrhagic trauma.

5. The method of claim 1 wherein the N-terminal BPI protein product is being administered to a subject to ameliorate adverse effects associated with burn injury.

6. The method of claim 1 wherein the subject being treated is suffering from a gram-negative bacterial infection.

7. The method of claim 1 wherein the subject being treated is suffering from a gram-positive bacterial or mycoplasmal infection.

8. The method of claim 1 wherein the subject being treated is suffering from a fungal infection.

9. The method of claim 1 wherein the subject being treated is suffering from a protozoan infection.

10. The method of claim 1 wherein the subject being treated is suffering from a chlamydial infection.

11. The method of claim 1 wherein the subject being treated is suffering from a mycobacterial infection.

12. The method of claim 1 wherein the subject being treated is suffering from a chronic inflammatory disease.

13. The method of claim 1 wherein the N-terminal BPI protein product is being administered to a subject to inhibit angiogenesis.

14. The method of claim 1 wherein the N-terminal BPI protein product is being administered to a subject to promote fibrinolysis.

15. The method of claim 1 wherein the N-terminal BPI protein product is an amino-terminal fragment of BPI protein having a molecular weight of about 20 kD to 25 kD.

16. The method of claim 1 wherein the BPI protein product is $rBPI_{23}$ or a dimeric form thereof.

17. The method of claim 1 wherein the BPI protein product is $rBPI_{21}$.

* * * * *

UNITED STATES PATENT AND TRADEMARK OFFICE
CERTIFICATE OF CORRECTION

PATENT NO.   : 6,482,796 B2
DATED        : November 19, 2002
INVENTOR(S)  : Carroll It is certified that error appears in the above-identified patent and that said Letters Patent is hereby corrected as shown below:

<u>Column 18,</u>
Line 46, after "10. The…" please delete "met ho d" and insert -- method -- in its place.

Signed and Sealed this

Thirteenth Day of May, 2003

JAMES E. ROGAN
*Director of the United States Patent and Trademark Office*